(12) United States Patent
Delfort et al.

(10) Patent No.: US 7,151,187 B2
(45) Date of Patent: Dec. 19, 2006

(54) PROCESS FOR TRANSESTERIFICATION OF VEGETABLE OILS OR ANIMAL OILS BY MEANS OF HETEROGENEOUS CATALYSTS BASED ON ZINC OR BISMUTH, TITANIUM AND ALUMINIUM

(76) Inventors: Bruno Delfort, 15 rue Broca, 75005 Paris (FR); Gérard Hillion, 10 place du Cassan, 95220 Herblay (FR); Dominique Le Pennec, 16 rue du Clos des Bourgognes, 78910 Orgerus (FR); Christophe Lendresse, 37 boulevard National, 92500 Rueil Malmaison (FR)

( * ) Notice: Subject to any disclaimer, the term of this patent is extended or adjusted under 35 U.S.C. 154(b) by 0 days.

(21) Appl. No.: 11/118,776

(22) Filed: May 2, 2005

(65) Prior Publication Data

US 2005/0261509 A1 Nov. 24, 2005

(30) Foreign Application Priority Data

May 3, 2004 (FR) .................................. 04 04730
May 3, 2004 (FR) .................................. 04 04731

(51) Int. Cl.
*C11C 1/00* (2006.01)
(52) U.S. Cl. ...................................... 554/167; 554/170
(58) Field of Classification Search ................ 554/167, 554/170
See application file for complete search history.

(56) References Cited

U.S. PATENT DOCUMENTS 5,908,946 A 6/1999 Stern et al.
6,147,196 A 11/2000 Stern et al.

FOREIGN PATENT DOCUMENTS

EP 0924185 6/1999

OTHER PUBLICATIONS

Peterson G R et al: "Rapeseed oil Transesteirification by Heterogenous Catalysis" Journal of the American Oil Chemists' Society, American Oil Chemists' Society. Champaign, US, vol. 61, No. 10, Oct. 1984 pp. 1593-1597, XP002170978.

*Primary Examiner*—Deborah D. Carr
(74) *Attorney, Agent, or Firm*—Millen, White, Zelano & Branigan, P.C.

(57) ABSTRACT

A new process for the production of linear monocarboxylic acid esters with 6 to 26 carbon atoms, by reaction of vegetable oils or animal oils that may or may not be neutral, with monoalcohols of 1 to 18 carbon atoms, uses a catalyst that is selected from among:

the combinations of zinc oxides and titanium oxides;
the combinations of zinc oxide, titanium oxide and alumina;
the combinations of bismuth and titanium oxides; and
the combinations of bismuth oxide, titanium oxide and alumina.

The process makes it possible to produce directly, in one or more stages, an ester that can be used as a fuel and a pure glycerin.

23 Claims, No Drawings

PROCESS FOR TRANSESTERIFICATION OF VEGETABLE OILS OR ANIMAL OILS BY MEANS OF HETEROGENEOUS CATALYSTS BASED ON ZINC OR BISMUTH, TITANIUM AND ALUMINIUM

This invention relates to a new process for the production of monocarboxylic acid esters from vegetable oils or animal oils.

The reaction that is the primary target is a transesterification that is carried out according to diagram I below and optionally a combined reaction of esterification and transesterification, whereby the esterification is carried out according to Diagram II below. In these diagrams, the fatty acid chains are arbitrarily shown by oleic-type chains.

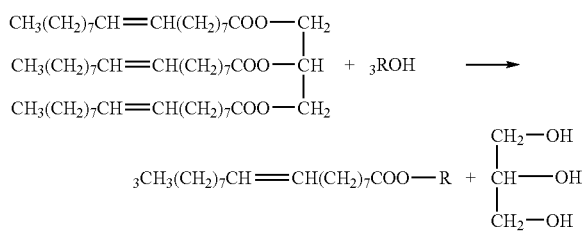

Diagram I

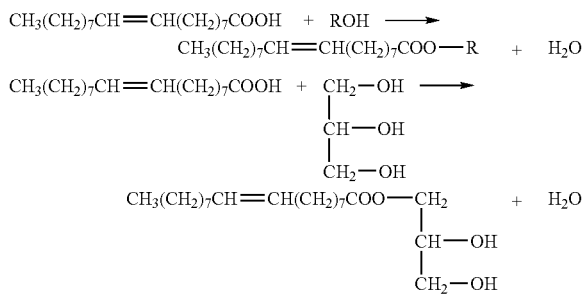

Diagram II

The fatty acid esters are currently used in numerous applications as diesel fuels, domestic fuels, solvents, basic compounds for the production of sulfonates of fatty alcohols, amides and ester dimers, etc.

When an ester is produced from oil and monoalcohol, it is formed automatically, according to the nature of the oil that is used at the beginning, from 10 to 15% of a secondary product, which is glycerin. This glycerin is sold at a high price for various uses, but only when it has high purity. The latter is obtained after intense purification in specialized units in vacuum distillation.

In the production of fatty-substance methyl esters from refined oils and alcohol, whereas simple alkaline derivatives, such as sodium alcoholates, soda or potash, are now used as catalysts under rather mild conditions (temperature from 50 to 80° C. and atmospheric pressure), and it is possible to read this in numerous patents or publications, for example in JAOCS 61, 343–348 (1984), it is only after numerous stages, however, that a pure product that can be used as a fuel and a glycerin is produced as prescribed by the standards.

If the most-used alkaline catalysts are assumed, for example, these alkaline compounds are found both in the glycerin and in the ester. It is necessary to eliminate them by washing and/or by neutralization in the ester fraction, then to dry the latter. In the glycerin phase, it is necessary to neutralize the soaps and the alcoholates that are present, sometimes eliminating the salts that are formed.

The glycerin that is thus obtained contains water, generally between 5% and 40% by mass. It also contains the salts that are obtained from the neutralization of the alkaline catalyst, for example sodium chloride when the catalyst is soda or sodium methylate, and when the neutralization is carried out with hydrochloric acid. The concentration of salts in the glycerin that is obtained from these processes is generally 3% to 6% by mass. Obtaining high-purity glycerol from the glycerine that is obtained from these processes therefore imposes purification stages such as the distillation under reduced pressure that can sometimes be associated with ion exchange resin treatments.

In summary, most of the commercial processes for production of esters culminate easily enough in crude products (esters and glycerin) that it is necessary to purify deeply, however, by various treatments that ultimately increase the price of the transformation.

It was now discovered, surprisingly enough, that it was possible to obtain in 1 to 3 stages, under particular conditions, directly from vegetable oils or animal oils and monoalcohols, esters of these monoalcohols and a glycerin that is free of salts, in any case that does not contain more than 5 ppm, with a purity of 95% to 99.9%, most often 98% to 99.9%, and this by using as catalysts either continuously, for example in a fixed bed, or intermittently, a particular heterogeneous catalytic system.

The use of heterogeneous catalysts is not new.

Among the prior documents that deal with heterogeneous catalysts, it is possible to cite European Patent EP-B-0 198 243. The transesterification catalyst, which transforms oil and methanol into methyl ester, is an alumina or a mixture of alumina and ferrous oxide. In the examples, the column that is used for the fixed bed has a volume of 10 liters, and oil is injected generally at a flow rate of less than 1 liter/hour, which provides a VVH (VVH=volume of injected oil/volume of catalyst/hour) that is less than 0.1. For a factory of 100,000 t/year, this would correspond to reactors of at least 150 m$^3$.

Another problem that seems to arise is that of the amount of collected glycerin, much smaller than in theory. The high reaction temperature (280° C. to 320° C.) causes a degradation of the glycerol. Examples indicate ether contents of glycerol of more than 80% relative to the glycerol that is formed. In none of the examples where the goal is to collect 10% glycerin is a value obtained that is even close to this. Finally, the purity of the esters is low enough, from 93.5 to 98%. In some cases, significant amounts of glycerin ethers are formed, as is reported in this patent; in other cases, it may decompose, unless it is eliminated in a first stage. The performance level is therefore quite low. It is possible to point out that with the VVH indicated and for a contact time of more than 6 hours, it is possible to obtain conversions of 80% and more even without a catalyst.

This patent therefore does not seem to exhibit a reasonable solution from the economic standpoint.

There are other references in the literature that this time mention zinc oxide, however, in esterification reactions of the glycerin with a fatty acid [Osman in "*Fette Seifen und Anstrichmittel [Fatty Soaps and Paints]*", 331–33 (1968)]. In this work, about 20 catalysts are compared at 180° C. in an intermittent process. There is virtually no difference between zinc chloride, zinc sulfate, zinc powder, barium oxide, calcium oxide, zinc oxide, alumina, thiosalicylic acid, calcium phosphate, potassium bicarbonate, sodium methylate or ethylate and even lithium hydroxide. All these salts or oxides provided a yield of monoglyceride of between 32 and 39% in a comparative test when excess glycerin is used relative to the fatty acid.

It is possible to cite Patent U.S. Pat. No. 5,908,946 that describes a process that can operate continuously or intermittently and that uses solid and insoluble catalysts. However, the catalysts that are used are either zinc oxide, or a mixture of zinc oxide and alumina, or a zinc aluminate.

This invention proposes a process for the production of at least one fatty acid ester and glycerin ester, whereby these two products are obtained with a high degree of purity, whereby this process can be defined generally by the fact that it is carried out, by reaction of acid or neutral vegetable or animal oils with monoalcohols, for example 1 to 18 carbon atoms, preferably 1 to 12 carbon atoms, and even more preferably 1 to 5 carbon atoms, by using at least one catalyst that is selected from among:

the combinations of zinc and titanium oxides;
the combinations of zinc oxides, titanium oxide and alumina;
the combinations of bismuth and titanium oxides; and
the combinations of bismuth oxide, titanium oxide and alumina.

The combinations of oxides that comprise zinc oxide, titanium oxide and optionally alumina more particularly correspond to the formula:

$$[(ZnO)_a—(TiO_2)_b]y[Al_2O_3]1-y$$

This formula can also take the form:

$$[Zn_aTi_bO_{(a+2b)}]y[Al_2O_3]1-y$$

(whereby a has a value of 0.5 to 5, b has the value of 0.5 to 5, and y has a value of 0.005 to 1, preferably 0.005 to 0.995).

The combinations of oxides that comprise bismuth oxide, titanium oxide and optionally alumina correspond more particularly to the formula:

$$[(Bi_2O_3)_a—(TiO_2)_b]y[Al_2O_3]1-y$$

(whereby a has the value of 0.5 to 5, b has the value of 0.5 to 5, and y has a value from 0.005 to 1, preferably 0.005 to 0.995).

The reaction conditions of the vegetable or animal oils with the monoalcohols preferably include a temperature of 150 to 250° C., and a pressure that is less than 100 bar and preferably 10 to 70 bar (it is recalled that 1 bar=0.1 MPa), by using excess monoalcohol relative to the oil/alcohol stoichiometry.

All the catalysts that are being considered are in the form of powder, balls, extrudates or pellets. The use of alumina has two favorable results. The first is to increase the specific surface area of the catalyst because the zinc oxide (or bismuth oxide), the titanium dioxide or the zinc titanite (or bismuth titanite) are known for having small specific surface areas. The second is to create a much more stable compound, primarily with regard to conditions in which the titanium compound and the zinc compound (or bismuth compound) would have a tendency to form titanium or zinc (or bismuth) soaps.

A major advantage of these solid catalysts is that they catalyze the reactions of transesterification and esterification according to a heterogeneous catalysis process, i.e., that the solid catalyst that is used, on the one hand, is not consumed in the reaction, and, on the other hand, is never dissolved in the reaction medium but remains in solid form and will therefore be separated from the liquid reaction medium without loss of catalyst and without polluting the reaction medium by the presence of catalyst or catalyst residue.

This is verified in the invention by the absence of traces obtained from the catalyst both in the ester that is formed as well as in the glycerin that is produced.

The feedstock of this catalyst is not affected by the transesterification or esterification reaction. Its catalytic activity is preserved after the reaction. This type of catalyst is compatible with use in a continuous industrial process, for example, in a fixed bed in which the catalyst feedstock can be used for a very long period without loss of activity.

The ester and the glycerol that are obtained do not contain impurities obtained from the catalyst. Thereby, no purification treatment will be applied to eliminate the catalyst or the residues of the latter, contrary to the processes that use catalysts that operate according to a homogeneous process, where the catalyst or its residues are, after reaction, located in the same phase as ester and/or glycerin.

By the implementation of this process, the final clean-up is reduced to a minimum, while making it possible to obtain an ester that meets specifications as a fuel and a glycerin of purity 95% to 99.9% and preferably between 98% and 99.9%.

The process of the invention is described in a more detailed manner below.

Among the oils that can be used in the process of the invention, it is possible to cite all the common oils, such as palm, palm nut, coconut, babassu, old or new colza, sunflower seed, corn, castor and cotton oil, the peanut oils, oils of linseed and cramble and all the oils that are obtained from, for example, sunflower seed or colza by genetic modification or hybridation.

It is even possible to use waste kitchen oils, varied animal oils, such as fish oils, tallow, lard, oils from the butchering of animals, and even fats.

Among the oils that are used, it is also still possible to indicate the oils that are partially modified by, for example, polymerization or oligomerization, such as, for example, the "stand oils" of linseed oils, sunflower seed oils and blown vegetable oils.

The presence of fatty acid in the oils is not a priori detrimental, other than that there is a risk of saponification. It is possible to provide a preliminary alycerolysis of the free fatty acid with a transesterification catalyst prior to the transesterification reaction to form, at atmospheric pressure under partial vacuum and at temperatures of 180 to 220° C., a total or partial glyceride starting from fatty acids.

The nature of the alcohol that is brought into play in the process of the invention plays an important role in the transesterification activity. In a general way, it is possible to bring into play various aliphatic monoalcohols that contain, for example, 1 to 18 carbon atoms, preferably 1 to 12 carbon atoms. The most active is methyl alcohol. Ethyl alcohol and the isopropyl, propyl, butyl, isobutyl and even amyl alcohols can be used, however. It is also possible to use heavier alcohols, such as the ethyl-hexyl alcohol or lauryl alcohol. It is advantageously possible to add methyl alcohol to heavy alcohols, which seems to facilitate the reaction. Furthermore, when ethyl ester is prepared, it is possible to bring into play 1 to 50%, preferably 1 to 10%, methyl alcohol so as to increase the conversion.

The preparation of catalysts based on titanium is not new. It is possible to cite Patent U.S. Pat. No. 4,490,479, which deals with the catalyst synthesis by co-mixing. In particular, the authors describe the addition of oxides, hydroxides, alkoxides or titanium salts to a precursor of alumina or to hydrated aluminum compounds. In the presence of water and mineral or organic acids, the mixture of the above-mentioned elements is carried out so as to form a paste. The latter is shaped so as to obtain a substrate. The addition of a molybdenum compound is also described in a second stage.

Patent U.S. Pat. No. 5,169,822 teaches the deposition of titanium alkoxides in a non-aqueous medium on inorganic substrates (among others).

The article by S. Kumar et al. in Mat. Lett. 43 (2000) 286 teaches the precipitation of a boehmite sol with a titanium dioxide sol. The titanium sol is prepared by stabilization with acetic acid.

To produce a catalyst of empirical formula $$[(ZnO)_a\text{—}(TiO_2)_b]y[Al_2O_3]1-y$$

whereby this formula can also take the form $$[Zn_aTi_bO_{(a+2b)}]y[Al_2O_3]1-y$$

(whereby a, b and y are defined as above), it is possible to use the following sources.

Among the zinc sources, it is possible to cite the oxide forms (ZnO), and the alkoxide forms [Zn(OR)$_2$, with R=Me, Et, Pr, iPr, Bu, iBu, etc.]. It is also possible to use zinc in the form of inorganic salts (ZnCl$_2$, etc.). Likewise, the colloidal forms of zinc can be used (by colloidal, the applicant means that the bismuth oxide particles are 1 nm to 100 nm in size). Finally, the zinc sources can be gels that are obtained from the hydrolysis of the preceding sources, thus obtaining a form of hydrated zinc oxide of chemical formula Zn(OH)$_2$.

To produce a catalyst of empirical formula:

$$[(Bi_2O_3)_a\text{—}(TiO_2)_b]y[Al_2O_3]1-y$$

(whereby a, b and y are defined as above), it is possible to use the following sources.

Among the bismuth sources, it is possible to cite the oxide forms (Bi2O3), and the alkoxide forms [Bi(OR)$_3$, with R=Me, Et, Pr, iPr, Bu, iBu, etc.]. It is also possible to use the bismuth in the form of inorganic salts (BiCl$_3$, BiOCl, etc.). Likewise, the colloidal forms of bismuth can be used. Finally, the bismuth sources can be gels that are obtained from the hydrolysis of the preceding sources, thus obtaining a bismuth hydroxide Bi(OH)$_3$ or a partially hydrated form of bismuth oxide with chemical formula Bi$_2$O$_3$, zH$_2$O, with z between 0 and 10. It is also advantageous to use the dehydrated, amorphous or crystallized bismuth oxide.

Among the titanium sources, it is possible to cite the oxide forms (TiO$_2$), and the alkoxide forms [Ti(OR)$_4$ with R=Me, Et, Pr, iPr, Bu, iBu, etc.]. It is also possible to use titanium in the form of inorganic salts (TiCl$_4$, TiOSO$_4$, TiOCl$_2$, etc.). Likewise, the colloidal forms of titanium can be used (by colloidal, the inventor means that titanium oxide or titanium oxyhydroxide particles are between 1 nm and 100 nm in size). Finally, the titanium sources can be gels that are obtained from the hydrolysis of the preceding sources, thus obtaining a partially hydrated form of titanium oxide with chemical formula TiO$_2$, zH$_2$O, with z between 0 and 5. It is also advantageous to use dehydrated, amorphous or crystallized titanium oxide that in this latter case has quadratic, monoclinical, or cubic crystallographic structures that are known by one skilled in the art.

Alumina Sources

The aluminum sources used in the invention can be in alkoxide form with general formula Al(OR)$_3$, with R=Me, Et, Pr, iPr, Bu, iBu, etc., or hydroxide. The inorganic aluminum salts can also advantageously be used, namely the chlorides, nitrates, sulfates, etc. Likewise, the aluminum source can be basic, in which case the aluminum is in aluminate form (AlO$_2$$^-$). The counter-ion can be alkaline (Li, Na, K, Cs) and more generally any positive counter-ion (NH4+, for example). In the case of the use of a solid aluminum precursor, any alumina compound of general formula Al$_2$O$_3$, nH$_2$O can be used. Its specific surface area is 100 to 600 m$^2$/g. It is possible in particular to use hydrated alumina compounds such as hydrargillite, gibbsite, bayerite, boehmite, pseudo-boehmite and amorphous or essentially amorphous alumina gels. It is also possible to use the dehydrated forms of these compounds that consist of transition aluminas and that comprise at least one phase taken from the group: rho, khi, eta, kappa, theta, delta, gamma and alpha, which differ essentially in the organization of their crystalline structure.

The catalyst advantageously can be prepared by one of the methods described below.

1. The impregnation of at least one soluble salt, of an alkoxide, of a sol or of an alkoxide on a preformed alumina substrate with a specific surface area of 20 to 600 m$^2$/g, preferably between 100 and 370 m$^2$/g. This substrate can be in the form of powder, balls, extrudates or any other form that is known to one skilled in the art and that makes it possible to work in a fixed bed, in a boiling bed, or in slurry. This substrate is selected from among the above-mentioned alumina sources. After various stages that are known to one skilled in the art, the catalysts are dried between 25° C. and 150° C., preferably between 50° C. and 120° C., then calcined at temperatures of between 150 and 1000° C., preferably between 250 and 600° C.

2. The mixing of at least one titanium compound and at least one zinc (or bismuth) compound with a more or less hydrated alumina compound, defined above as a solid precursor in the presence of a peptizing agent (mineral acid or organic acid). The peptizing agents are preferably nitric and acetic acids. It can also be added to the paste that is obtained from known agents to facilitate the shaping such as the methyl cellulose-type derivatives or any other compounds that are known to one skilled in the art for this purpose. The product is then shaped by extrusion, then dried between 40 and 150° C., preferably between 70 and 120° C., then calcined at temperatures of between 300 and 1100° C., preferably between 350 and 800° C.

3. The synthesis via sol-gel path between a zinc (or bismuth) alkoxide, a titanium alkoxide and an aluminum alkoxide, selected from among the sources that are cited above, preferably, for aluminum, sec-butoxide; for zinc, isopropoxide; for bismuth, pentyloxide; and, for titanium, isopropoxide. These precursors can be mixed in the presence of a suitable solvent and optionally a complexing agent or surfactants. The unit can be hydrolyzed so as to obtain a gel. The gel can be dried between 40 and 140° C., preferably between 80 and 130° C., and shaped by standard extrusion techniques with optional addition of binder, either by putting it back in suspension in a suitable liquid to form balls by "oil-drop" precipitation, or pelletized. In all the cases, the shaped objects are dried between 40 and 150° C., preferably between 70 and 120° C., then calcined at temperatures of between 300° C. and 1100° C., preferably between 350 and 800° C.

4. The co-precipitation between at least one zinc (or bismuth) salt, a sol or a zinc (or bismuth) alkoxide, at least one titanium salt, a sol or a titanium alkoxide and at least one salt, a sol or an aqueous aluminum alkoxide. The co-precipitation may take place in the presence only of water or agents that promote precipitation, such as an inorganic base (soda, potash, sodium carbonate, ammonia, hydrazine, etc.) or an organic base (urea, etc.) or an inorganic acid (nitric acid, sulfuric acid, etc.) or an organic acid (formic acid, acetic acid, etc.). The precipitation should therefore take place at a pH of between 4 and 13 as it is known to one skilled in the art, more preferably between pH 5 and 9. The co-precipitate is filtered and washed carefully based on the nature of the precursors and agents so as to limit the alkaline ion contents (sodium, potassium, etc.) to less than 0.5% and preferably to less than 0.1% by mass relative to the oxides. Likewise, the contents of anions (chloride, sulfide, etc.) should be limited to less than 1%, preferably less than 0.3% by mass. The precipitate that is obtained can be sprayed, then shaped by extrusion, by pelletizing or by resuspending in a suitable solvent to form balls. In all the cases, the objects that are shaped are dried between 40 and 150° C., preferably between 70 and 120° C., then calcined at temperatures of between 300 and 1100° C., preferably between 350 and 800° C.

Regardless of the preparation method retained, it is preferable to have a titanium oxide content of at least 10% by mass, preferably 23% by mass, and even more preferably 50% by mass. To the extent possible, the titanium dioxide should be found in primarily amorphous or micro-crystallized form, remarkable in this by the absence on the X-ray diffraction diagram of lines relative to the crystallized forms of titanium dioxide that are known by one skilled in the art.

Relative to the texture of the catalyst, it is important to maintain the specific surface area measured by the BET method that is known to one skilled in the art and the pore volume at correct values. The catalyst thus will have in general a specific surface area of 10 to 500 $m^2/g$, preferably 30 to 400 $m^2/g$, and more preferably 40 to 300 $m^2/g$. Likewise, the pore volume will be between 0.1 $cm^3/g$ and 1.2 $cm^3/g$, and preferably more than 0.2 $cm^3/g$. Finally, the pore distribution will be 0.001 to 0.1 micrometer.

If the transesterification is carried out in the absence of catalyst, either in an autoclave or in a fixed bed with inert substrates, such as silicon carbide, it is possible to obtain, at certain temperatures that are generally more than or equal to 250° C., conversions that exceed 80%, but with very low VVH and with very long dwell times. The thermal reaction therefore exists, and it is sometimes difficult to decide between the catalytic effect and the thermal effect, which explains that with simple aluminas, it is possible to obtain high conversions. The purpose of the process of the invention is, however, to obtain these conversions with reasonable dwell times, therefore with reasonable VVH.

The operating conditions that are used clearly depend on the process that is selected. If there is recourse to an intermittent reaction, it is possible to work in one or two stages, e.g., to produce a first reaction up to 85% to 95% of conversion, to cool by evaporating excess monoalcohol (for example, methanol), to decant the glycerin and to finish the reaction by reheating again and by adding alcohol to obtain a total conversion. It is also possible to target a conversion of 98% by working long enough in a single stage.

If a continuous reaction is undertaken, it is possible to work with several autoclaves and decanters. In the first, a conversion of, for example, 85%, is carried out, then it is decanted by evaporating the alcohol and by being cooled; in a second reactor, the transesterification reaction is achieved by adding a portion of the alcohol that was previously evaporated. Finally, excess alcohol is evaporated in an evaporator, and the glycerin and the esters are separated by decanting.

If a continuous process in a fixed bed is selected, it is advantageously possible to work at temperatures of 150 to 250° C., preferably 170 to 210° C., at pressures of 30 to 70 bar, if methyl esters are produced, whereby the VVH is preferably 0.1 to 3, preferably 0.3 to 2, in the first stage, and the alcohol/oil mass ratio varies from 3/1 to 0.1/1.

The introduction of the alcohol can advantageously be fractionated. The introduction at two levels into the tubular reactor can be carried out in the following way: supply of the reactor with oil and about ⅔ of the alcohol to be brought into play, then introduction of additional alcohol approximately at the upper third of the catalytic bed.

If 220° C. is not exceeded, generally an ester of the same color as the departing oil and a colorless glycerin are obtained after decanting. The ester and/or glycerin can be passed over a resin, an earth and/or activated carbon. The ester can also be purified either by distillation or by washing with methanolic glycerin to reduce its monoglyceride content.

The analysis of the compounds that have been produced is done either by gas phase chromatography for the esters and the glycerin, or, more quickly, by liquid chromatography by exclusion for the esters. It is noted that the process of the invention, conversely to known processes carried out in basic catalysis that is homogeneous with monoalcohols, produces only very few sterol esters. The sterol esters, which are heavy products, can create deposits in the injectors.

The examples that are presented below do not limit the invention and are used only to illustrate it.

Synthesis of Catalysts

Catalyst 1

It consists of a preformed alumina substrate in the form of balls with diameters of 1.4 mm, a specific surface area SBET=189 $m^2/g$, and a pore volume V=0.6 $cm^3/g$ is used.

Catalyst 2

Catalyst 2 is prepared by impregnation of zinc isopropoxide and titanium isopropoxide in catalyst 1. The alumina is calcined at 400° C. for 1 hour, then, after returning to ambient temperature, 23 g of zinc isopropoxide and 23 g of titanium isopropoxide are mixed with 5 ml of heptane, then poured slowly on 85 g of alumina. The unit is stirred for 24 hours. The solid that is obtained is placed in ambient air for 72 hours, then dried in an oven. The catalyst is calcined at 500° C. for 4 hours. The analysis by X-ray diffraction shows the presence of a crystalline phase, characteristic of the presence of gamma-alumina. No line that is characteristic of the rutile phases or anatase is detected. The specific surface area that is measured by the BET method is 141 $m^2/g$. The contents of zinc and titanium that are measured by X fluorescence are respectively 8.4 and 4.0% by mass.

Catalyst 3

Catalyst 3 is prepared by co-mixing. 30 g of boehmite (Pural SB3) is mixed with 35 g of titanium gel $TiO_2$, and 35 g of zinc oxide ZnO in the presence of 3 g of nitric acid at 70% and 45 g of water. The components are mixed for 1 hour to form a paste. The paste that is thus obtained is converted into extrudates that have diameters of 1.6 mm and that are dried at 150° C. for 20 hours and calcined in air at 600° C. for 3 hours.

The specific surface area that is measured by the BET method is 62 $m^2/g$. The content of aluminum, zinc and titanium that is measured by X fluorescence is respectively 14%, 24%, and 17% by mass.

Catalyst 4

Catalyst 4 is prepared by impregnation of bismuth pentyloxide and titanium isopropoxide in catalyst 1. The alumina is calcined at 400° C. for 1 hour, then, after retuning to ambient temperature, 15 g of bismuth pentyloxide and 27 g of titanium isopropoxide are mixed with 5 ml of heptane, then poured slowly over 80 g of alumina. The unit is stirred for 24 hours. The solid that is obtained is placed in ambient air for 72 hours, then dried in an oven. The catalyst is calcined at 500° C. for 4 hours. The analysis by X-ray diffraction shows the presence of a crystalline phase that is characteristic of the presence of gamma-alumina. No line that is characteristic of the rutile or anatase phases is detected. The specific surface area that is measured by the BET method is 148 m$^2$/g. The contents of bismuth and titanium, measured by X fluorescence, are respectively 13.5 and 4.6% by mass.

Catalyst 5

Catalyst 3 is prepared by co-mixing. 30 g of boehmite (Pural SB3) is mixed with 18 g of titanium gel $TiO_2$ and 51 g of bismuth oxide $Bi_2O_3$ in the presence of 3 g of nitric acid at 70% and 45 g of water. The components are mixed for 1 hour to form a paste. The paste that is thus obtained is converted into extrudates with diameters of 1.6 mm that are dried at 150° C. for 20 hours and calcined in air at 600° C. for 3 hours.

The specific surface area that is measured by the BET method on the catalyst that is obtained is 54 m$^2$/g. The contents of aluminum, bismuth and titanium, measured by X fluorescence, are respectively 13%, 23%, and 3.7% by mass.

EXAMPLE 1

(For Comparison) Reaction in the Absence of Catalyst 25 g of colza oil, whose composition is presented in detail in the table below, and 25 g of methanol are introduced into a 100 ml autoclave reactor that is equipped with a stirring system and a temperature and pressure control.

| Fatty Acid Glyceride | Nature of the Fatty Chain | % by Mass |
|---|---|---|
| Palmitic | C16:0 | 5 |
| Palmitoleic | C16:1 | <0.5 |
| Stearic | C18:0 | 2 |
| Oleic | C18:1 | 59 |
| Linoleic | C18:2 | 21 |
| Linoleic | C18:3 | 9 |
| Arachidic | C20:0 | <0.5 |
| Gadoleic | C20:1 | 1 |
| Behenic | C22:0 | <0.5 |
| Erucic | C22:1 | <1 |

The medium is brought to 200° C. while being stirred. The pressure reaches 32 bar.

Samples are taken after 2 hours, 5 hours and 7 hours. In each sample, after excess methanol evaporates, the glycerol that is formed by decanting is eliminated, and the methyl ester concentration is determined by steric exclusion chromatography. It is respectively 18%, 36% and 52%.

EXAMPLE 2

Reaction in the Presence of Catalyst 3

25 g of colza oil, whose composition is presented in detail in Example 1, 25 g of methanol and 1 g of catalyst 3 are introduced into a 100 ml autoclave reactor that is equipped with a stirring system and a temperature and pressure control. The medium is brought to 200° C. while being stirred. The pressure reaches 32 bar.

Samples are taken in the liquid phase after 2 hours, 5 hours and 7 hours of reaction. In each sample, after the excess methanol is filtered and evaporated, then glycerol that is formed by decanting is eliminated, the methyl ester concentration is determined by steric exclusion chromatography. It is respectively 66%, 77% and 87%.

The concentrations of zinc, titanium and aluminum in the methyl ester that is obtained are less than 1 ppm. The concentrations of zinc, titanium and aluminum in the glycerol that is obtained are less than 1 ppm. These results confirm the heterogeneous nature of the catalysis.

This makes possible the use of the catalyst in a process for preparation of fuel esters without having to initiate an additional treatment for purification of the methyl ester to eliminate the traces of residual catalyst.

Under the same conditions, the same recycled catalyst leads to a methyl ester concentration of 87% after 7 hours of reaction, which indicates that the catalyst is not degraded at all and that it has preserved all its activity. This operation was repeated twice more and led to the same conclusions.

EXAMPLE 3

Example 2 is repeated, this time by using 150 g of colza oil, 150 g of methanol, and 25 g of catalyst 3.

The reaction is conducted at 200° C. for 8 hours. After the excess methanol is filtered and then evaporated, followed by the elimination of the glycerol that is formed by decanting, the methyl ester concentration, determined by steric exclusion chromatography, is 94%.

The concentrations of zinc, titanium and aluminum in the methyl ester that is obtained are less than 1 ppm. The concentrations of zinc, titanium and aluminum in the glycerol that is obtained are less than 1 ppm. These results confirm the heterogeneous nature of the catalysis.

Under the same conditions, the same recycled catalyst leads to a methyl ester concentration of 93.5% after 7 hours of reaction, which indicates that the catalyst is not degraded at all and that it preserves all its activity.

EXAMPLE 4

Reaction in the Presence of Catalyst 5

Example 2 is repeated by using 1 g of catalyst 5.

Samples are taken in the liquid phase after 2 hours, 5 hours and 7 hours of reaction. In each sample, after the excess methanol is filtered and evaporated and then the glycerol that is formed by decanting is eliminated, the methyl ester concentration is determined by steric exclusion chromatography. It is respectively 66%, 78% and 88%.

The concentrations of bismuth, titanium and aluminum in the methyl ester that is obtained are less than 1 ppm. The concentrations of bismuth, titanium and aluminum in the glycerol that is obtained are less than 1 ppm. These results confirm the heterogeneous nature of the catalysis.

This makes possible the use of the catalyst in a process for preparation of ester fuel without having to initiate an additional treatment for purification of methyl ester to eliminate the traces of residual catalyst.

Under the same conditions, the same recycled catalyst leads to a methyl ester concentration of 88% after 7 hours of reaction, which indicates that the catalyst is not degraded at all and that it has preserved all its activity. This operation was repeated twice more and led to the same conclusions.

EXAMPLE 5

Example 4 is repeated, this time by using 150 g of colza oil, 150 g of methanol and 25 g of catalyst 5.

The reaction is conducted at 200° C. for 8 hours. After excess methanol is filtered and then evaporated, followed by the elimination of the glycerol that is formed by decanting, the methyl ester concentration, determined by steric exclusion chromatography, is 94%.

The concentrations of bismuth, titanium and aluminum in the methyl ester that is obtained are less than 1 ppm. The concentrations of bismuth, titanium and aluminum in the glycerol that is obtained are less than 1 ppm. These results confirm the heterogeneous nature of the catalysis.

Under the same conditions, the same recycled catalyst leads to a methyl ester concentration of 93% after 7 hours of reaction, which indicates that the catalyst is not degraded at all and that it preserved all its activity.

EXAMPLES 6 TO 8

Methanolysis is carried out in a device that comprises a fixed-bed reactor, i.e., a filled column, with a diameter that is equal to 1.9 cm and a length that is equal to 120 cm, heated by 3 shells that surround the column. The preheating of the oil and the methanol is done in the column on 10 cm³ of glass balls, and the reaction on 70 cm³ of volume of catalyst 3. At the outlet of the column, 20 cm³ of tungsten carbide and 5 cm³ of glass balls are added. The device in the shape of an upside-down U consists of a tubular reactor, a cooling on the horizontal portion and a decanter, which constitutes the second branch. On the upper portion of the decanter, a gas purging system makes it possible to regulate the pressure, i.e., to keep the latter initially with the nitrogen at the desired pressure of 15 to 60 bar. The decanter has a liquid purge at its lower outlet. When the decanter is half-full, an automatic valve opens to partially empty the product that is obtained. Two pumps inject alcohol and oil into the column from bottom to top at selected flow rates and with constant pressure.

The reaction products are collected after 24 hours of passage at the desired VVH (VVH=oil volume/catalyst volume/hour).

After having drawn off the product that consists of methanol, glycerol and ester, generally present in a single phase, the methanol is evaporated, then the ester and the glycerol are separated by decanting.

The analysis of the ester is done by steric exclusion chromatography. The results are therefore those that are obtained without any final purification, if it is not that that consists in evaporating the excess methanol and in separating the ester from the glycerin by decanting, preferably toward 50° C.

The following table presents the results that are obtained after 24 hours of reaction.

The VVH is the volume of oil injected per volume of catalyst and per hour. The ratio R is the ratio of oil/alcohol volume, noted H/A. The pressure is the prevailing pressure in the decanter, expressed in bar.

The composition of the mixture is expressed in % by mass.

The contact time takes into account the presence of methanol: it is determined by the equation:

$$\text{Contact time} = \frac{70 \text{ cm}^3 \text{ of catalyst} \times 60(*)}{\text{Volume of cm}^3 \text{ of oil} + \text{injected alcohol in 1 hour}}$$

(*) 60 = time in minutes.

In the table:
E=esters (also contains sterols)
MG=monoglycerides
DG=diglycerides that do not contain esters of sterols, because they do not form from them under these conditions
TG=triglycerides

| | Methanolysis of Colza Oil with Catalyst 3 | | | | | | | |
|---|---|---|---|---|---|---|---|---|
| Example | T (° C.) | VVH | Vol/Vol H/A Ratio | P (bar) | TG (%) | DG (%) | MG (%) | E (%) | t of contact (min) |
| 6 | 200 | 0.5 | 1 | 50 | 0.9 | 2.1 | 3.3 | 93.7 | 60 |
| 7 | 200 | 0.5 | 1.5 | 50 | 4.3 | 2.7 | 4.1 | 88.9 | 72 |
| 8 | 180 | 0.5 | 1 | 50 | 3.3 | 5.1 | 7.5 | 84.1 | 60 |

Analyses of zinc and titanium by X fluorescence were carried out on the methyl esters and the glycerol that were obtained. The absence of zinc and titanium in these products confirms the heterogeneous nature of the catalysis.

EXAMPLE 9

The procedure of Examples 6 to 8 is repeated by replacing the colza oil that is used as a feedstock by a mixture of esters whose composition is identical to that obtained in Example 6.

The composition of the ester phase that is obtained is:

| Methyl esters: | 99.3% |
|---|---|
| Monoglycerides: | 0.6% |
| Diglycerides: | 0.1% |
| Triglycerides: | not detected |

This composition is compatible with the specifications that are required for an ester fuel for diesel engines.

EXAMPLES 10 TO 12

Examples 6 to 8 are repeated by using the catalyst of Example 5.

The conditions are indicated in the table below.

Methanolysis of the Colza Oil with Catalyst 5

| Example | T (° C.) | VVH | Vol/Vol H/A Ratio | P (bar) | TG (%) | DG (%) | MG (%) | E (%) | t of contact (min) |
|---|---|---|---|---|---|---|---|---|---|
| 10 | 200 | 0.5 | 1 | 50 | 0.8 | 1.7 | 3.0 | 94.5 | 60 |
| 11 | 200 | 0.5 | 1.5 | 50 | 3.6 | 2.8 | 3.6 | 90.0 | 72 |
| 12 | 180 | 0.5 | 1 | 50 | 2.9 | 5.1 | 7.1 | 84.9 | 60 |

Analyses of bismuth and titanium by X fluorescence have been carried out on the methyl esters and the glycerol that were obtained. The absence of bismuth and titanium in these products confirms the heterogeneous nature of the catalysis.

EXAMPLE 13

The procedure of Examples 10 to 12 is repeated by replacing the colza oil that is used as a feedstock by a mixture of esters whose composition is identical to the one that is obtained in Example 10.

The composition of the ester phase that is obtained is:

| Methyl esters: | 99.5% |
| Monoglycerides: | 0.4% |
| Diglycerides: | 0.1% |
| Triglycerides: | not detected |

This composition is compatible with the specifications that are required for an ester fuel for diesel engines.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding French application No. 04/04.730, filed May 3, 2004, and French application No. 04/04.731, filed May 3, 2004, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for the production of at least one ester of fatty acid and glycerin with a high degree of purity, comprising reacting a vegetable or animal oil with an aliphatic monoalcohol containing 1 to 18 carbon atoms, in the presence of at least one catalyst selected from the group consisting of:
   a combination of zinc and titanium oxides,
   a combination of zinc oxide, titanium oxide and alumina,
   a combination of bismuth and titanium oxides, and
   a combination of bismuth oxide, titanium oxide and alumina.

2. A process according to claim 1, wherein said aliphatic monoalcohol contains 1 to 12 carbon atoms.

3. A process according to claim 1, wherein said aliphatic monoalcohol contains 1 to 5 carbon atoms.

4. A process according to claim 1, conducted at a temperature of between 150° C. and 250° C., under a pressure of less than 100 bar and with excess monoalcohol relative to the oil/alcohol stoichiometry.

5. A process according to claim 1, wherein said catalyst is in the form of powder, extrudates or balls.

6. A process according to claim 1, wherein the catalyst has a surface area of 10 to 500 $m^2/g$, a pore volume of 0.1 to 1.2 $cm^3/g$, and a pore distribution of 0.01 to 0.1 micrometer.

7. A process according to claim 6, wherein the catalyst has a surface area of 30 to 400 $m^2/g$ and a pore volume of more than 0.2 $cm^3/g$.

8. A process according to claim 1, wherein said reacting is conducted intermittently.

9. A process according to claim 1, wherein said reacting is conducted continuously, either in a fixed bed, or with autoclaves and decanters in series.

10. A process according to claim 9, wherein said reacting is conducted in a fixed bed, with a VVH of 0.1 to 3.

11. A process according to claim 1, comprising conducting successively:
   an initial transesterification with a conversion of the oil into ester of at least 85%;
   a first evaporation of excess monoalcohol;
   decanting of the glycerin and ester, and recycling said ester into a second stage to undergo a transesterification with a portion of the monoalcohol recovered in the first evaporation;
   a second evaporation of the monoalcohol, decanting under cold conditions and separating the glycerin and the ester.

12. A process according to claim 1, wherein the initial oil is an acidic oil, and a preliminary glycerolysis of the free fatty acid with a transesterification catalyst, at a temperature of between 180 and 220° C., and at a pressure equal to or less than 1 bar.

13. A process according to claim 1, wherein the ester that is obtained is purified by passage over a resin, an earth and/or activated carbon.

14. A process according to claim 1, wherein the ester that is obtained is purified either by distillation or by washing with methanolic glycerin to reduce its monoglyceride content.

15. A process according to claim 11, wherein the glycerin that is obtained after the alcohol is evaporated is ultimately purified by passage over a resin, an earth and/or activated carbon.

16. A process according to claim 1, wherein to produce an ethyl ester, ethyl alcohol is used in a mixture with a proportion of 1 to 50% methanol.

17. A process according to claim 1, wherein the catalyst corresponds to the formula:

$$[(ZnO)_a\text{---}(TiO_2)_b]y[Al_2O_3]1-y,$$

wherein a has a value of 0.5 to 5, b has a value of 0.5 to 5, and y has a value of 0.005 to 1.

18. A process according to claim 17, wherein in the formula:

$$[(ZnO)_a\text{---}(TiO_2)_b]y[Al_2O_3]1-y$$

y has a value of 0.005 to 0.995.

19. A process according to claim 1, wherein the catalyst corresponds to the formula:

$$[(Bi_2O_3)_a\text{---}(TiO_2)_b]y[Al_2O_3]1-y,$$

wherein a has a value of 0.5 to 5, b has a value of 0.5 to 5, and y has a value of 0.005 to 1.

20. A process according to claim 19, wherein in the formula:

$$[(Bi_2O_3)_a\text{---}(TiO_2)_b]y[Al_2O_3]1-y,$$

y has a value of 0.005 to 0.995.

21. A process according to claim 1, wherein the catalyst corresponds to the formula:

$$[Zn_aTi_bO_{(a+2b)}]y[Al_2O_3]1-y,$$

wherein a has a value of 0.5 to 5, b has a value of 0.5 to 5, and y has a value of 0.005 to 1.

22. A process according to claim 21, wherein in the formula:

$$[Zn_aTi_bO_{(a+2b)}]y[Al_2O_3]1-y,$$

y has a value of 0.005 to 0.995.

23. A process according to claim 10, wherein said VVH is 0.3 to 2.

* * * * *

UNITED STATES PATENT AND TRADEMARK OFFICE
CERTIFICATE OF CORRECTION

PATENT NO. : 7,151,187 B2  Page 1 of 1
APPLICATION NO. : 11/118776
DATED : December 19, 2006
INVENTOR(S) : Bruno Delfort It is certified that error appears in the above-identified patent and that said Letters Patent is hereby corrected as shown below:

Column 15, line 17, reads "$[(ZnO)_a\text{-}(TiO_2)_b/y[Al_2O_3]1\text{-}y$" should read -- $[(ZnO)_a\text{-}(TiO_2)_b]y[Al_2O_3]1\text{-}y$ --
Column 15, line 23, reads "$[(ZnO)_a\text{-}(TiO_2)_b/y[Al_2O_3]1\text{-}y$" should read -- $[(ZnO)_a\text{-}(TiO_2)_b]y[Al_2O_3]1\text{-}y$ --
Column 16, line 3, reads "$[(Bi_2O_3)_a\text{-}(TiO_2)_b/y[Al_2O_3]1\text{-}y$" should read -- $[(Bi_2O_3)_a\text{-}(TiO_2)_b]y[Al_2O_3]1\text{-}y$ --
Column 16, line 9, reads "$[(Bi_2O_3)_a\text{-}(TiO_2)_b/y[Al_2O_3]1\text{-}y$" should read -- $[(Bi_2O_3)_a\text{-}(TiO_2)_b]y[Al_2O_3]1\text{-}y$ --
Column 16, line 14, reads "$[Zn_aTi_bO_{(a+2b)}/y[Al_2O_3]1\text{-}y$" should read -- $[Zn_aTi_bO_{(a+2b)}]y[Al_2O_3]1\text{-}y$ --
Column 16, line 20, reads "$[Zn_aTi_bO_{(a+2b)}/y[Al_2O_3]1\text{-}y$" should read -- $[Zn_aTi_bO_{(a+2b)}]y[Al_2O_3]1\text{-}y$ --

Signed and Sealed this

Tenth Day of July, 2007

JON W. DUDAS
*Director of the United States Patent and Trademark Office*